(12) United States Patent
Kato

(10) Patent No.: US 12,213,768 B2
(45) Date of Patent: Feb. 4, 2025

(54) BIOLOGICAL INFORMATION MEASUREMENT DEVICE

(71) Applicant: Sapporo Medical University, Hokkaido (JP)

(72) Inventor: Yuichi Kato, Hokkaido (JP)

(73) Assignee: Sapporo Medical University, Hokkaido (JP)

( * ) Notice: Subject to any disclaimer, the term of this patent is extended or adjusted under 35 U.S.C. 154(b) by 920 days.

(21) Appl. No.: 17/042,814

(22) PCT Filed: Mar. 28, 2019

(86) PCT No.: PCT/JP2019/013643
§ 371 (c)(1),
(2) Date: Sep. 28, 2020

(87) PCT Pub. No.: WO2019/189596
PCT Pub. Date: Oct. 3, 2019

(65) Prior Publication Data
US 2021/0015378 A1     Jan. 21, 2021

(30) Foreign Application Priority Data

Mar. 29, 2018   (JP) ................................. 2018-064067

(51) Int. Cl.
*A61B 5/024*     (2006.01)

(52) U.S. Cl.
CPC ...... *A61B 5/02427* (2013.01); *A61B 5/02438* (2013.01); *A61B 2560/0406* (2013.01)

(58) Field of Classification Search
CPC .... A61B 2560/0406; A61B 2562/0238; A61B 5/02427; A61B 5/02433; A61B 5/02438;
(Continued)

(56) References Cited

U.S. PATENT DOCUMENTS

| 2009/0275813 A1 | 11/2009 | Davis |
| 2009/0281435 A1 | 11/2009 | Ahmed et al. |

(Continued)

FOREIGN PATENT DOCUMENTS

| CH | 669101 A5 | 2/1989 |
| JP | 2011-519634 A | 7/2011 |

(Continued)

OTHER PUBLICATIONS

International Search Report and Written Opinion for International Application No. PCT/JP2019/013643 filed on Mar. 28, 2019.

*Primary Examiner* — Michael T Rozanski
(74) *Attorney, Agent, or Firm* — K&L Gates LLP; Brian J. Novak; Giorgios N. Kefallinos

(57) ABSTRACT

The biological information measurement device (100) includes: a clip (110) that is attached on the scapha of an auricle in such a way as to clamp the scapha from both sides; and a pulse wave sensor (120) that is disposed on a portion of the clip (110), is arranged in such a way as not to compress the helix when the clip (110) is attached on the scapha of the auricle, and measures biological information of an artery running in the helix. The pulse wave sensor (120) may be a non-contact type sensor that measures the biological information, using transmitted light, and the clip (110) may be configured in such a way that the pulse wave sensor (120) does not come into contact with the helix when the clip (110) is attached in such a way as to clamp the scapha of the auricle from both sides.

16 Claims, 17 Drawing Sheets

(58) Field of Classification Search
CPC . A61B 5/0261; A61B 5/0295; A61B 5/14552; A61B 5/6815; A61B 5/6838
See application file for complete search history.

(56) References Cited

U.S. PATENT DOCUMENTS

| | | |
|---|---|---|
| 2011/0245662 A1 | 10/2011 | Eggers et al. |
| 2015/0038808 A1 | 2/2015 | Shimuta |
| 2016/0051147 A1 | 2/2016 | Cohen et al. |
| 2016/0081562 A1 | 3/2016 | Lachhman |
| 2018/0035933 A1 | 2/2018 | Ho et al. |

FOREIGN PATENT DOCUMENTS

| | | |
|---|---|---|
| JP | 2013-533753 A | 8/2013 |
| JP | 2017-038911 A | 2/2017 |
| WO | 2013/161729 A1 | 10/2013 |
| WO | 2014/061139 A1 | 9/2016 |
| WO | 2016/160478 A1 | 10/2016 |
| WO | 2017/091107 A1 | 6/2017 |
| WO | 2018/107198 A1 | 6/2018 |
| WO | 2019/189596 A1 | 10/2019 |

0°

5°

15°

BIOLOGICAL INFORMATION MEASUREMENT DEVICE

CROSS REFERENCE TO RELATED APPLICATION(S)

This application is a national phase filing of PCT/JP2019/013643, filed on Mar. 28, 2019, which claims priority to Japanese Patent Application No. 2018-064067, filed on Mar. 29, 2018, the entire disclosures of which are incorporated herein by reference.

TECHNICAL FIELD

The present disclosure relates to a biological information measurement device.

BACKGROUND ART

Biological information measurement devices (wearable devices) that are capable of constantly measuring biological information while being attached on a subject have been known. In, for example, Patent Literature 1, a biological information measurement device that includes a clip attachable on the lobule of ear and a sensor detecting biological information, such as blood volume and a pulse rate, is disclosed.

CITATION LIST

Patent Literature

Patent Literature 1: International Publication No. WO 2014/061139

SUMMARY OF INVENTION

Technical Problem

In the case of the biological information measurement device in Patent Literature 1, when a portion of the lobule of ear is clamped by the clip, the sensor for detecting blood volume, a pulse rate, and the like is pressed against the lobule of ear and arteries in the lobule of ear at which blood volume, a pulse rate, and the like of the living body are to be detected are also compressed at the same time. Thus, there is a problem in that it is difficult for the biological information measurement device in Patent Literature 1 to measure biological information, such as blood volume and a pulse rate, of a living body accurately.

The present disclosure has been made based on the foregoing circumstances, and an objective of the disclosure is to provide a biological information measurement device that is capable of accurately measuring biological information from an artery running in an auricle even when the biological information measurement device is attached on the auricle.

Solution to Problem

In order to achieve the above-described objective, a biological information measurement device according to the present disclosure includes:
attachment means attached on a scapha of an auricle in such a way as to clamp the scapha from both sides; and
measurement means disposed on a portion of the attachment means, arranged in such a way as not to compress a helix of an auricle when the attachment means is attached on a scapha of the auricle, and measuring biological information of an artery running in the helix.

The measurement means may include a non-contact type sensor that measures biological information, using transmitted light, and
the attachment means may be configured in such a way that the measurement means does not come into contact with a helix of an auricle when the attachment means is attached in such a way as to clamp a scapha of the auricle from both sides.

The measurement means may include a pulse wave sensor that measures a pulse wave in an artery running in a helix.

The attachment means may be a clip that is attachable in such a way that a tip end portions of the clip clamp a scapha of an auricle from both sides, and
the measurement means may be disposed further on a base end side than a tip end side of the clip and measure biological information in an artery running in a helix.

The attachment means may include a first member and a second member that are connected to each other at base end portions of the first member and the second member and that are capable of clamping a scapha of an auricle from both sides between tip end portions of the first member and the second member, and
the measurement means may include a light emitting element that is disposed on the second member and that radiates light and a light receiving element that is disposed on the second member in such a way as to face the light emitting element and that receives transmitted light that is radiated from the light emitting element and transmitted through a measurement target site.

The second member may include:
a base end portion that is joined to the first member in a rotatable manner;
a first sensor support portion that is disposed on a base end side of the base end portion, that extends in a vertical direction with respect to the base end portion, and that supports the light emitting element;
a second sensor support portion that is disposed on a tip end side of the base end portion, that extends in a vertical direction with respect to the base end portion, and that supports the light receiving element in a direction in which the light receiving element faces the light emitting element; and
a tip end portion that is disposed on a tip end side of the second sensor support portion, that extends in a same direction as the second sensor support portion, and that, in conjunction with a tip end portion of the first member, clamps a scapha of an auricle from both sides.

The first member may include elastic deformation means that is disposed on a tip end portion of the first member and that is elastically deformed in accordance with a shape of a scapha of an auricle when the elastic deformation means comes into contact with the scapha of the auricle.

Advantageous Effects of Invention

The present disclosure enables a biological information measurement device that is capable of accurately measuring biological information from an artery running in an auricle even when the biological information measurement device is attached on the auricle to be provided.

DESCRIPTION OF EMBODIMENTS

Hereinafter, a biological information measurement device according to an embodiment of the present disclosure will be described with reference to the drawings. In the respective drawings, the same signs are assigned to the same or equivalent constituent elements.

Figure 1:
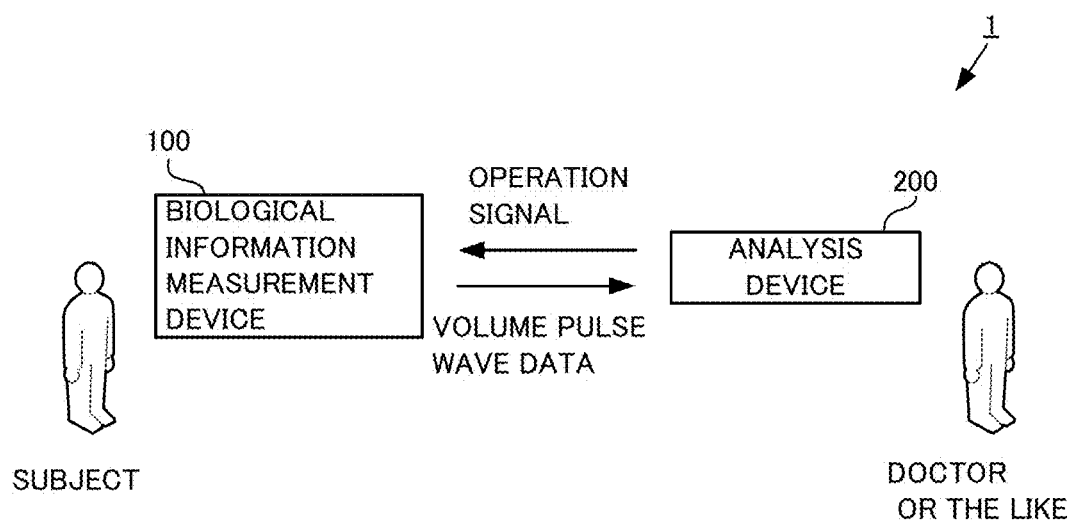
FIG. 1 is a block diagram illustrating a configuration of a biological information measurement system according to an embodiment of the present disclosure.

With reference to FIG. 1, a configuration of a biological information measurement system 1 according to the present embodiment will be described. FIG. 1 is a block diagram illustrating a configuration of the biological information measurement system 1. The biological information measurement system 1 measures a pulse wave from an artery in living tissue of a subject, calculates various types of data, such as a pulse rate and percutaneous oxygen saturation (SpO2), based on the measured pulse wave, and provides a user, such as a doctor, with the calculated data.

A pulse wave is a waveform that captures changes in the pulse in an artery, the changes being generated in association with blood being pumped out of the heart. Pulse waves include a pressure pulse wave the form of which represents changes in the internal pressure of an artery and a volume pulse wave the form of which represents changes in the volume of an artery. The biological information measurement system 1 according to the present embodiment measures a volume pulse wave in an artery that runs inside one of the auricles.

The biological information measurement system 1 includes a biological information measurement device 100 and an analysis device 200. The biological information measurement device 100 and the analysis device 200 are interconnected in a communicable manner via a communication line, such as the Internet.

The biological information measurement device 100 is a wearable device that can be attached on one of the auricles of the subject and that is capable of measuring a volume pulse wave in the auricle. The biological information measurement device 100 measures a volume pulse wave in an artery running inside the auricle and transmits volume pulse wave data relating to the measured volume pulse wave to the analysis device 200, based on an operation signal from the analysis device 200.

The analysis device 200 supplies the biological information measurement device 100 attached on the subject with an operation signal and, in conjunction therewith, acquires volume pulse wave data from the biological information measurement device 100, calculates various types of data, such as a pulse rate and SpO2, and supplies a user, such as a doctor, with the calculated data. A user, such as a doctor, who works in a medical institution can monitor cardiovascular status of a subject who is in a home care environment or the like, using the biological information measurement system 1.

Figure 2:
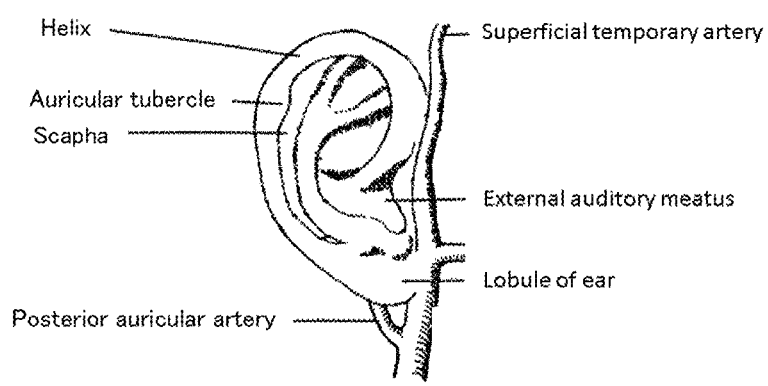
FIG. 2 is a diagram illustrating an anatomical structure of an auricle.

To facilitate understanding, an anatomical structure of one of the auricles will be described with reference to FIGS. 2 and 3 before describing the biological information measurement device 100. FIG. 2 is a diagram illustrating an appearance of one of the auricles when the auricle is observed from the front. The auricle is a portion of one of the ears that projects to the outside. A portion that extends from an upper end portion toward a back end portion of the auricle in a curved manner and that is bent toward the inner side is a "helix", and a portion that is adjacent to the helix on the external auditory meatus side is a "scapha". Below the "helix", an "auricular tubercle" is formed. A portion that hangs at a lower end portion of the auricle is a lobule of ear. Although the lobule of ear moves during conversation, the helix has a characteristic of being immobile even during conversation.

Inside the auricle, a posterior auricular artery (PAA) and a superficial temporal artery (STA), both of which extend from an external carotid artery, run vertically. The STA is a blood vessel that runs inside the helix, and the PAA is a blood vessel that runs inside the scapha (Ulusal BG, et al., Anatomical and technical aspects of harvesting the auricle as a neurovascular facial subunit transplant in humans, Plast Reconstr Surg, 2007 November, 120(6), 1540-1545). Since the STA and the PAA run in sites that are independent of each other, compressing one of the arteries never influences measurement of biological information in the other artery. Since a comparatively thick arterial vessel having a diameter of approximately 40 μm runs in a surface portion of the helix (Zilinsky I, et al., The arterial blood supply of the helical rim and the earlobe-based advancement flap (ELBAF): a new strategy for reconstructions of helical rim defects, J Plast Reconstr Aesthet Surg, 2015 January, 68(1), 56-62), the helix is an extremely useful site to measure a pulse wave signal.

Figure 3:
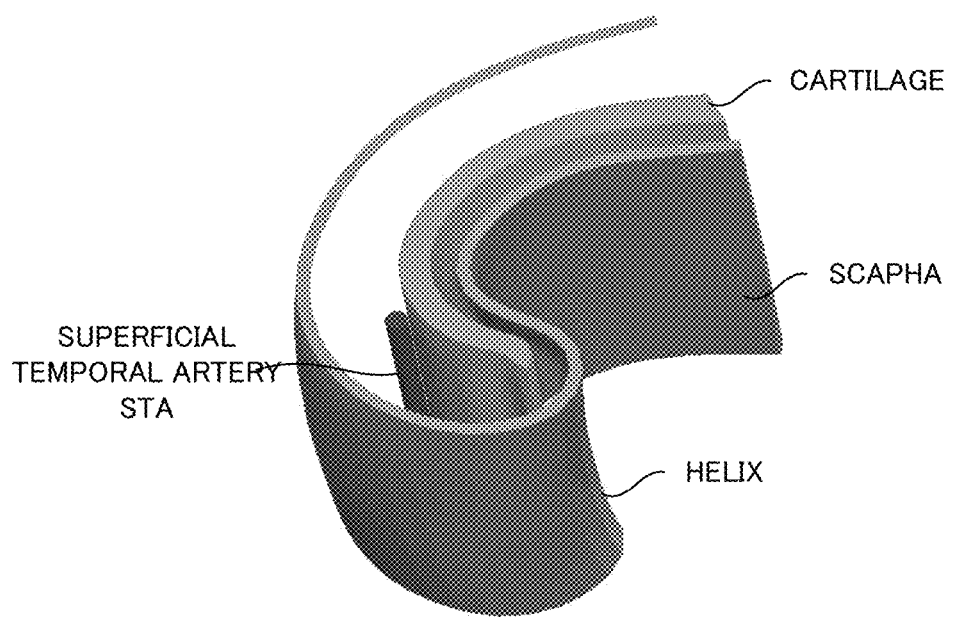
FIG. 3 is a cross-sectional view of a portion of the auricle in FIG. 2 taken along a cross-section including a helix and a scapha.

FIG. 3 is a cross-sectional view of a portion of the auricle in FIG. 2 taken along a cross-section including the helix and the scapha. As understandable from FIG. 3, since cartilage exists inside the scapha of the auricle and the cartilage extends to the helix, the tissue, arteries, and veins of the helix are never compressed even when the scapha is clamped from both sides. A configuration of the biological information measurement device 100 will be described below using as an example a case where the biological information measurement device 100 clamps the scapha of one of the auricles from both sides, thereby being attached on the auricles and, in conjunction therewith, measures a volume pulse wave in the superficial temporal artery inside the helix.

Figure 4:
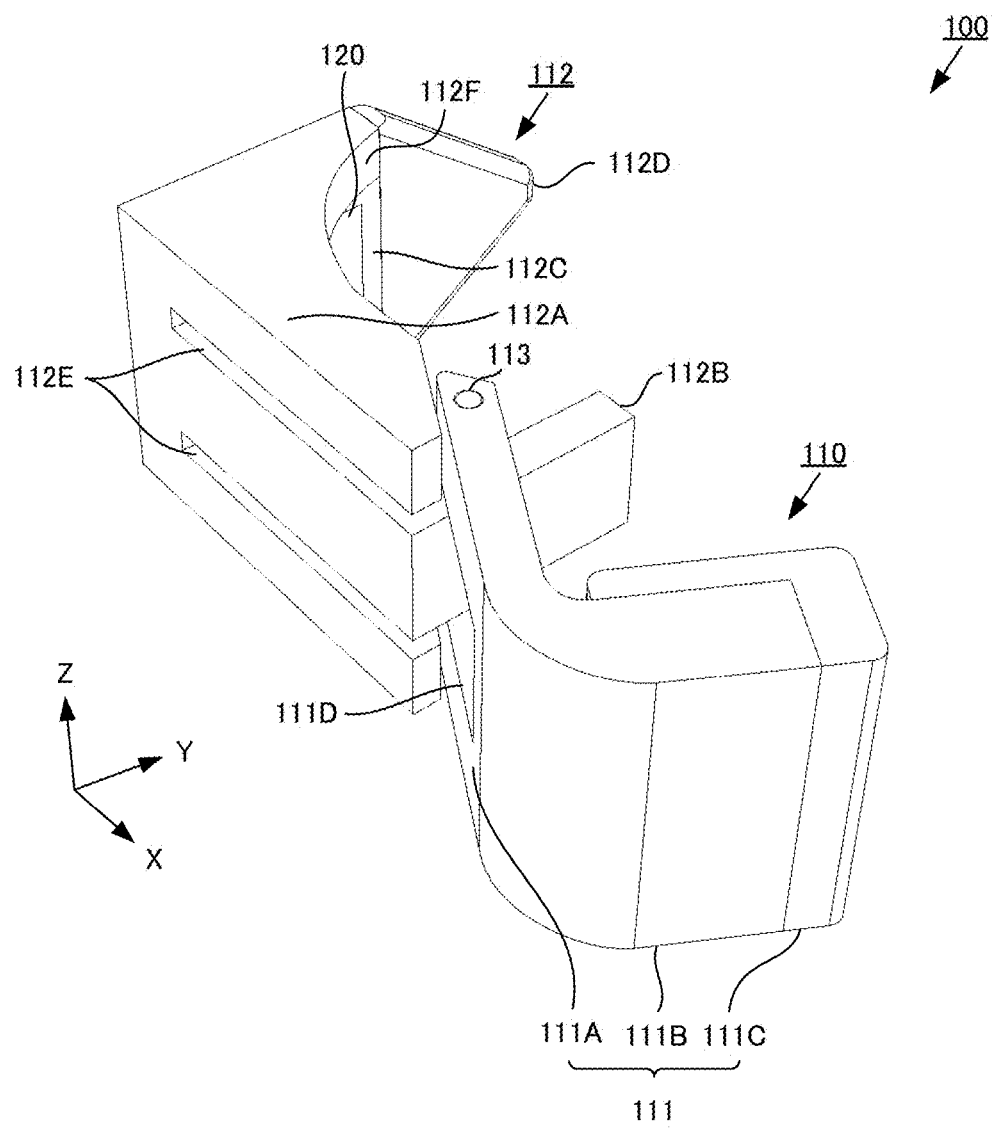
FIG. 4 is a perspective view illustrating a configuration of an outer face of a biological information measurement device according to the embodiment of the present disclosure.
Figure 5:
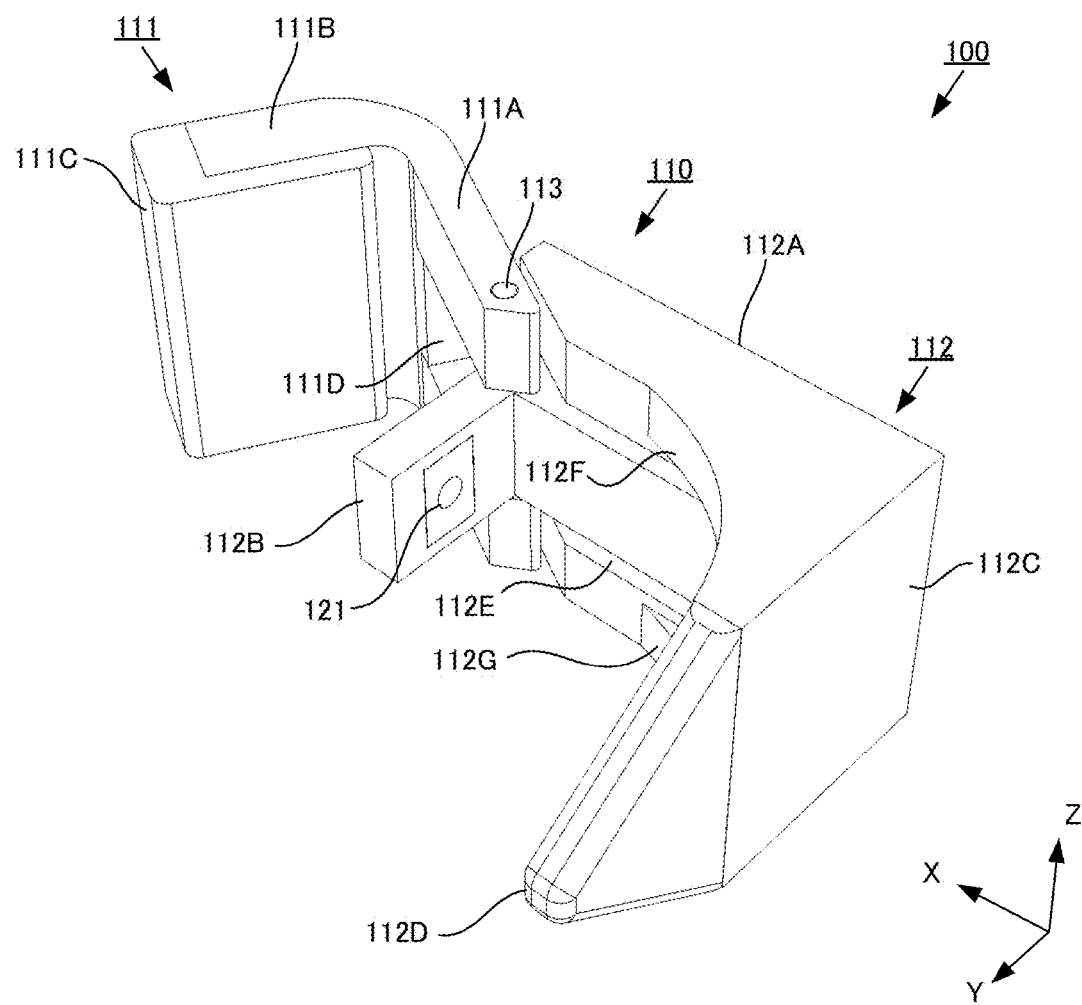
FIG. 5 is a perspective view illustrating a configuration of an inner face of the biological information measurement device according to the embodiment of the present disclosure.
Figure 6:
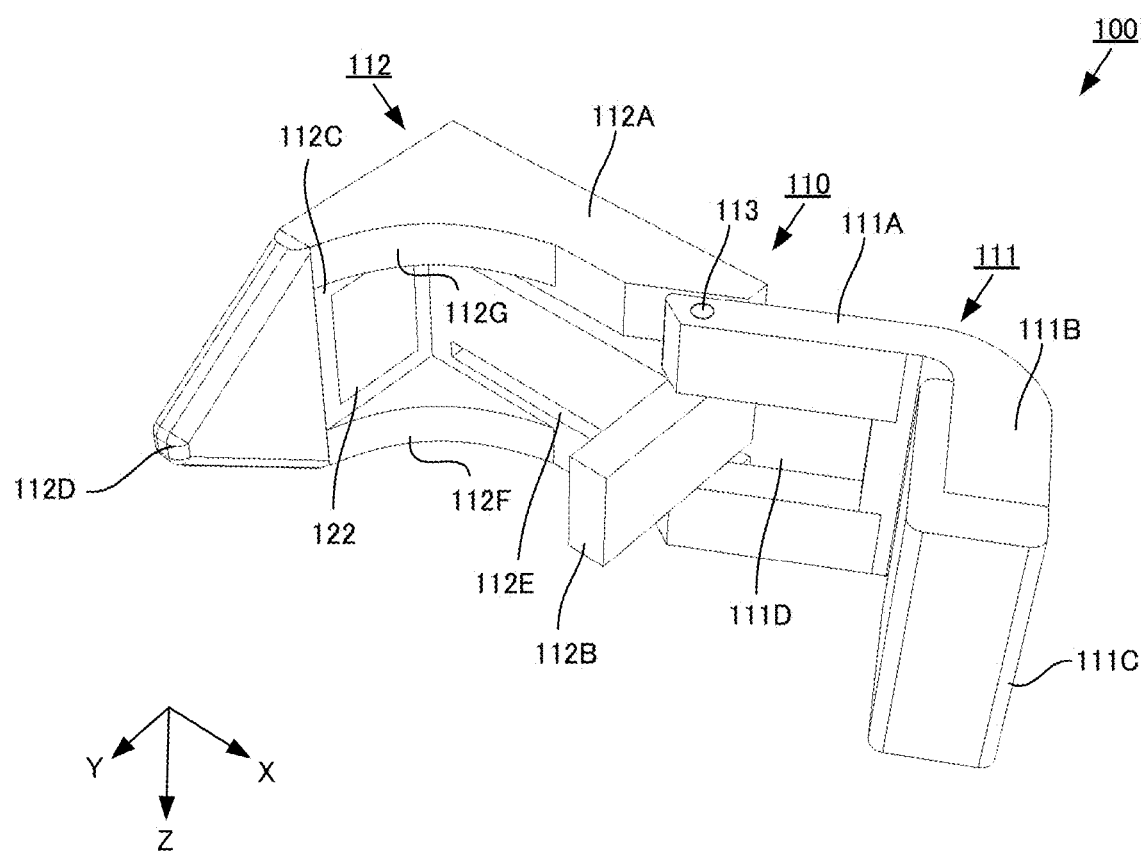
FIG. 6 is a perspective view of the biological information measurement device illustrated by vertically inverting the biological information measurement device in FIG. 5.
Figure 7:
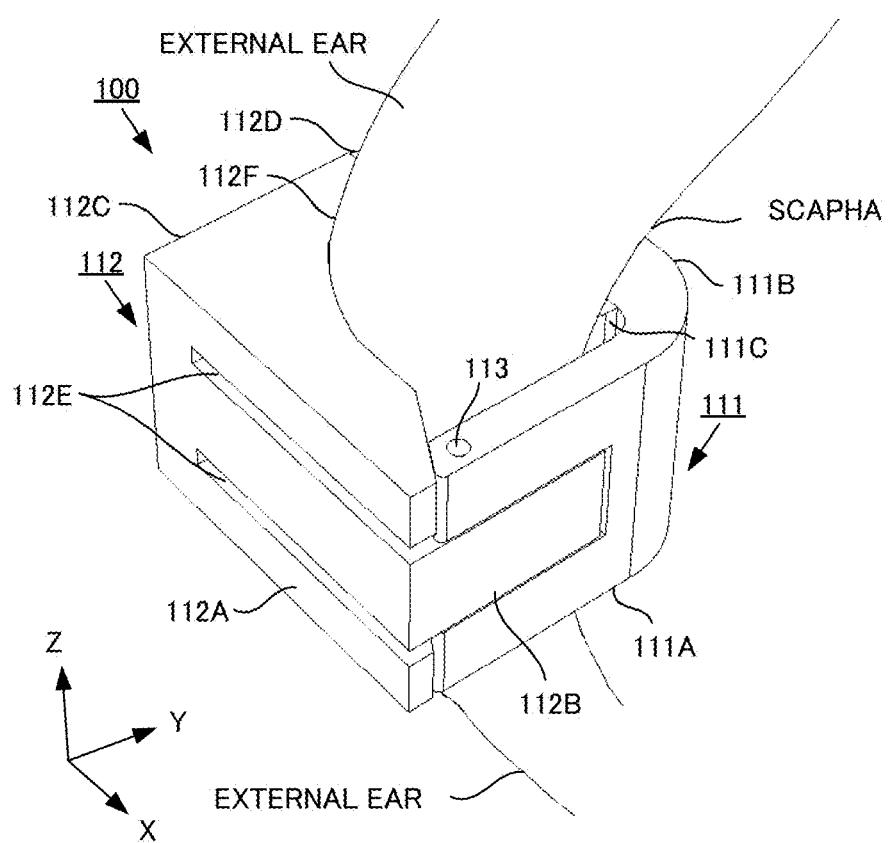
FIG. 7 is a diagram illustrating an appearance of the biological information measurement device according to the embodiment of the present disclosure attached on an auricle.

FIG. 4 is a perspective view illustrating a configuration of an outer face of the biological information measurement device 100, which is visible from the outside when the biological information measurement device 100 is attached on the auricle, and each of FIGS. 5 and 6 is a perspective view illustrating a configuration of an inner face of the biological information measurement device 100, which is invisible from the outside when the biological information measurement device 100 is attached on the auricle. The biological information measurement device 100 in FIG. 6 is illustrated by vertically inverting the biological information measurement device 100 in FIG. 5. FIG. 7 is a perspective view illustrating an appearance of the biological information measurement device 100 attached on one of the auricles. The biological information measurement device 100 includes a clip 110 that clamps one of the auricles of a subject, a pulse wave sensor 120 that is disposed on the clip 110 and that measures a volume pulse wave in the artery of the auricle, a communication antenna (not illustrated) that transmits volume pulse wave data from the pulse wave sensor 120 to the analysis device 200, and a battery (not illustrated) that supplies the pulse wave sensor 120 and the communication antenna with power.

The clip 110 is an example of attachment means that is attachable on one of the auricles of the subject in such a manner as to clamp the auricle. The clip 110 is configured not to compress a measurement target site at which a volume pulse wave is measured by the pulse wave sensor 120 and is configured to clamp an attachment target site that is located at a different position from that of the measurement target site. More specifically, the clip 110 is configured such that, when the clip 110 clamps the scapha, which is an attachment target site, from both sides, thereby being attached on the scapha, the pulse wave sensor 120 measures a volume pulse wave in the artery (STA) in the helix, which is a measurement target site and is located apart from the scapha.

It is assumed that cases of "not compressing" a measurement target site include not only a case of not compressing the measurement target site at all (pressure on the measurement target site is zero) but also a case of compressing the measurement target site to the extent of not affecting measurement of a volume pulse wave (for example, pressure on the measurement target site is equal to or less than 10 mmHg). The pulse wave sensor 120 may be arranged in such a way as to come into contact with the measurement target site or arranged apart from the measurement target site. In other words, the pulse wave sensor 120 may be a contact type sensor that is capable of measuring a biological signal of an artery by coming into contact with a portion of a living body or a non-contact type sensor that is capable of measuring a biological signal of an artery even without coming into contact with a portion of a living body.

The clip 110 includes a first member 111, a second member 112 that is supported in a rotatable manner via a rotation shaft 113 with respect to the first member 111, a spring (not illustrated) that biases the first member 111 and the second member 112 in such a way that a tip end portion of the first member 111 and a tip end portion of the second member 112 come close to each other. The first member 111 and the second member 112 are configured to be biased by the spring, thereby clamping the auricle from both sides by the tip end portions thereof. Hereinafter, regarding both the first member 111 and the second member 112, the side on which the rotation shaft 113 is disposed and the side apart from the rotation shaft 113 are referred to as "base end side" and "tip end side", respectively.

The first member 111 includes a base end portion 111A to which the second member 112 is joined in a rotatable manner, a tip end portion 111B that is disposed on the tip end side of the base end portion 111A and that is formed in such a way as to extend in the vertical direction with respect to the base end portion 111A, and a cushion 111C that is supported by the tip end portion 111B and that is arranged in such a way as to come into contact with one of the auricles. The base end portion 111A and the tip end portion 111B are shaped into an L-shape as a combined whole, and the outer side surface of a connecting portion (bent portion) of the base end portion 111A and the tip end portion 111B is formed in a curved manner in such a manner as to draw a gentle circular arc.

The base end portion 111A includes a pair of extended portions that extend in parallel with each other toward the base end side and is formed into a substantially U-shape as a whole. In each of tip end portions of the pair of extended portions, a through-hole through which the rotation shaft 113 can be inserted is formed. The rotation shaft 113 being inserted through the through-holes causes the base end portion 111A to be supported in a rotatable manner about the rotation shaft 113 that is fixed to the second member 112. The base end portion 111A has a space 111D formed at a central portion thereof, the space 111D housing a first sensor support portion 112B, which will be described later, of the second member 112. Thus, when the first member 111 is bent with respect to the second member 112, the first sensor support portion 112B enters the space 111D, as a result of which the first member 111 is never prevented from rotating with respect to the second member 112.

The cushion 111C is an example of elastic deformation means that comes into contact with the auricle and that is elastically deformed in accordance with the shape of the auricle. The cushion 111C is formed of a resin material, such as polyurethane, and is formed into an L-shape as a whole in such a way as to cover a surface on the tip end side and a surface on the inner side of the tip end portion 111B. A portion of the cushion 111C that extends from the tip end side of the tip end portion 111B is formed in such a way as to compress the scapha, which is an attachment target site, when the auricle is clamped by the first member 111 and the second member 112. A portion of the cushion 111C that is disposed on the inner side surface of the tip end portion 111B comes into contact with the inner side of the helix, thereby being deformed and restricts the clip 110 from moving to the outside of the auricle. Thus, when the auricle is clamped by the first member 111 and the second member 112, the clip 110 can be fixed in such a way as not to come off the attachment target site of the auricle even when the subject moves his/her body during free activity in daily life.

The second member 112 includes a base end portion 112A to which the first member 111 is joined in a rotatable manner, the first sensor support portion 112B that is disposed at an end portion on the base end side of the base end portion 112A and that supports a light emitting element of the pulse wave sensor 120, a second sensor support portion 112C that is disposed at an end portion on the tip end side of the base end portion 112A and that supports a light receiving element of the pulse wave sensor 120, and a tip end portion 112D that is disposed in such a manner as to extend from the tip end side of the second sensor support portion 112C and that comes into contact with the auricle, thereby clamping the auricle in combination with the cushion 111C. Hereinafter, to facilitate understanding, a Cartesian coordinate system with the X-axis, Y-axis, and Z-axis set in a direction in which the base end portion 112A extends, a direction in which the first sensor support portion 112B and the second sensor support portion 112C extend, and the up-and-down direction of the second member 112, respectively is used.

The base end portion 112A is a member that supports the first sensor support portion 112B and the second sensor support portion 112C respectively at opposite end portions of the base end portion 112A that are apart in the X-axis direction. In the base end portion 112A, a pair of slits 112E that extend in the X-axis direction and that are aligned in the Z-axis direction are formed. The pair of slits 112E penetrate the base end portion 112A from the outer side surface toward the inner side surface and are formed in parallel with each other. Humidity that is generated from the auricle is discharged from the inside of the clip 110 to the outside of the clip 110 through the pair of slits 112E.

The first sensor support portion 112B supports a light emitting element 121 of the pulse wave sensor 120. The first sensor support portion 112B is formed on a YZ plane in such a way as to extend in the vertical direction with respect to the base end portion 112A from a portion that is located on the base end side of the base end portion 112A and that is sandwiched by the pair of slits 112E.

The second sensor support portion 112C supports a light receiving element 122 of the pulse wave sensor 120. The second sensor support portion 112C is formed on a YZ plane in such a way as to extend in the vertical direction with respect to the base end portion 112A from the tip end side of the base end portion 112A. The first sensor support portion 112B and the second sensor support portion 112C are arranged facing each other. Thus, the base end portion 112A, the first sensor support portion 112B, and the second sensor support portion 112C are formed into a substantially U-shape when observed from the Z-axis direction.

The tip end portion 112D is an example of clamping means that clamps an attachment target site in combination with the cushion 111C. The tip end portion 112D is formed on a YZ plane in such a way as to extend in the same direction as that of the second sensor support portion 112C, that is, in the vertical direction with respect to the base end portion 112A from a tip end portion of the second sensor support portion 112C. The tip end portion 112D has a triangular shape that is formed in such a manner as to gradually narrow from the base end portion thereof toward the tip end portion thereof. Since the tip end portion 112D is configured to come into contact with one of the auricles, side edge portions thereof are chamfered and the tip end portion thereof is rounded.

The second member 112 further includes a pair of auricle contact portions 112F and 112G that respectively extend on XY planes in parallel with each other from edges of the base end portion 112A and the second sensor support portion 112C and that come into surface contact with the auricle. The auricle contact portions 112F and 112G have inner side surfaces thereof, which come into contact with the auricle, formed into recessed curved surfaces in accordance with the shape of the auricle. Thus, the auricle contact portions 112F and 112G are capable of positioning the clip 110 to a predetermined position of the auricle and, in conjunction therewith, preventing the attitude of the clip 110 attached on the auricle from tilting.

The first member 111 (except the cushion 111C) and the second member 112 are formed of, for example, a resin material and preferably formed of a white resin material. The reason why it is preferable to form the first member 111 (except the cushion 111C) and the second member 112, using a white resin material is to prevent infrared rays, red light, or the like radiated from the light emitting element of the pulse wave sensor 120 from being absorbed by the first member 111 and the second member 112 and affecting measurement of a pulse wave.

The spring is an example of biasing means that biases the first member 111 and the second member 112 in such a way as to make the first member 111 and the second member 112 come close to each other. The spring is, for example, a plate spring. The spring is configured to make the clip 110 clamp the auricle with elastic force strong enough not to cause the clip 110 to come off the auricle even when a body motion occurs while the subject performs a daily activity.

The pulse wave sensor 120 is an example of measurement means that measures a volume pulse wave in an artery, using photo-plethysmography. The pulse wave sensor 120 is, for example, a transmission-type photo-plethysmography sensor that measures a volume pulse wave by irradiating a body surface with infrared rays, red light, or the like and detecting the light amount of infrared rays, red light, or the like that is transmitted through the body. The pulse wave sensor 120 is disposed on the clip 110 in such a way as to perform measurement at a measurement target site that is located at a position different from that of an attachment target site that is clamped by the clip 110.

Figure 8:
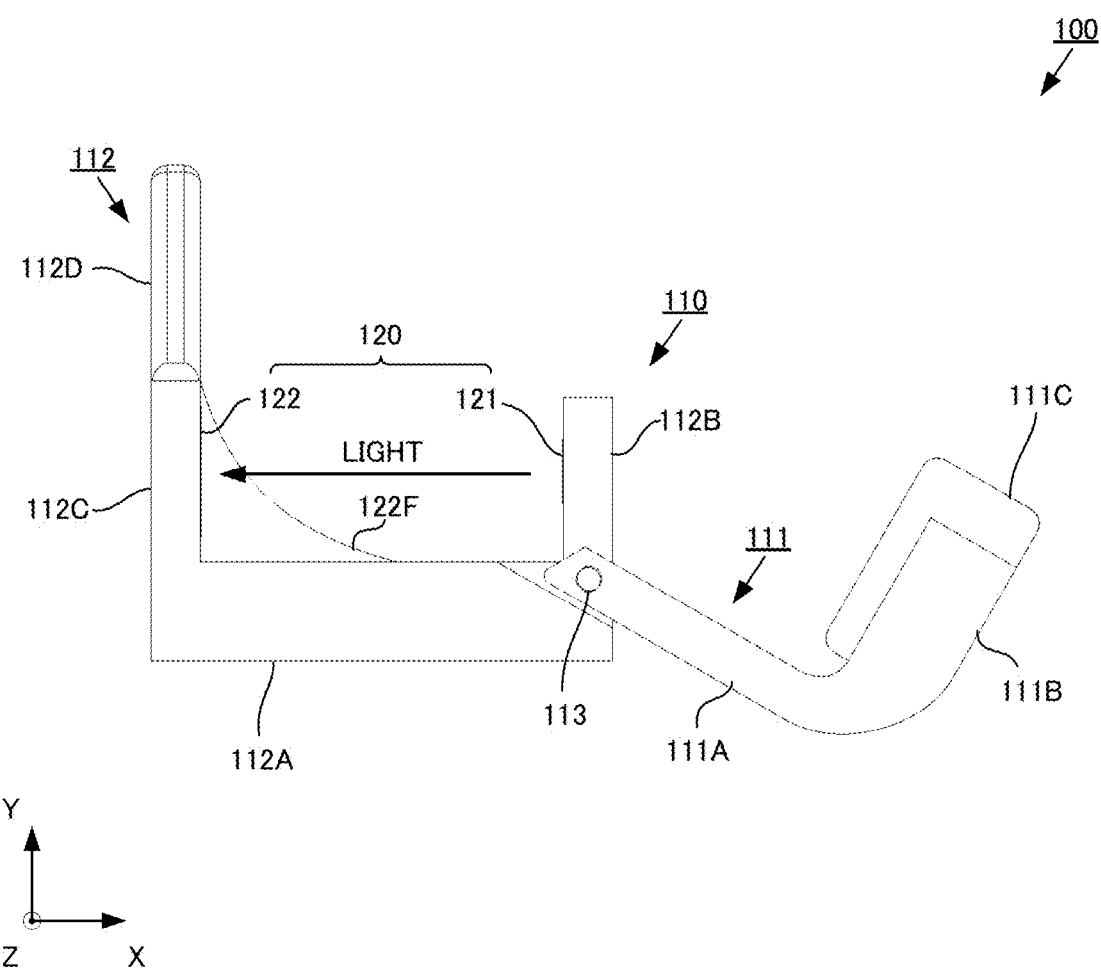
FIG. 8 is a plane view illustrating an appearance of the biological information measurement device according to the embodiment of the present disclosure observed from above.

FIG. 8 is a plane view of the biological information measurement device 100 observed from the Z-axis direction. The pulse wave sensor 120 includes the light emitting element 121 that radiates infrared rays, red light, or the like toward the auricle and the light receiving element 122 that receives transmitted light that is radiated from the light emitting element 121 and transmitted through the auricle. The light emitting element 121 is, for example, a light emitting diode (LED) that radiates infrared rays, red light, or the like and is configured to flash at a constant cycle.

The light receiving element 122 is, for example, a photodiode or a phototransistor that receives infrared rays, red light, or the like. The light receiving element 122 amplifies an electric signal that is generated by receiving transmitted light and provides the communication antenna of the biological information measurement device 100 with data to which the amplified electric signal is analog/digital (A/D) converted.

The light emitting element 121 and the light receiving element 122 are supported on the inner side surfaces of the first sensor support portion 112B and the second sensor support portion 112C, which are arranged on YZ planes, facing each other, respectively. Thus, the positional relationship between the light emitting element 121 and the light receiving element 122 never changes, in whatever direction with respect to the auricle the clip 110 is attached.

The pulse wave sensor 120 measures a photo-plethysmogram (PG), using the Lambert-Beer law. According to the Lambert-Beer law, when light is linearly transmitted through a solution of one layer, absorptance $I/I_0$ of the light is proportional to concentration C of the solution and depth D of the solution layer through which the light passes. Therefore, the absorptance $I/I_0$ of the light is expressed by the formula below, assuming that a mean absorption coefficient in consideration of arteries and veins is denoted by E. Note that I denotes intensity of transmitted light and $I_0$ denotes intensity of radiated light.

$$I/I_0 = \exp(-\varepsilon CD) \quad (1)$$

The intensity $I_0$ of radiated light is defined according to the light emitting element 121, and the mean absorption coefficient c and the concentration C of the solution are defined according to a measurement target site and concentration of blood. The intensity I of transmitted light is measured by the light receiving element 122. Thus, the depth D of the solution layer can be calculated using the formula (1). Calculating a blood volume in the artery, based on the depth D of the solution layer calculated using the formula (1) enables a volume pulse wave to be acquired as a plethysmogram.

Figure 9:
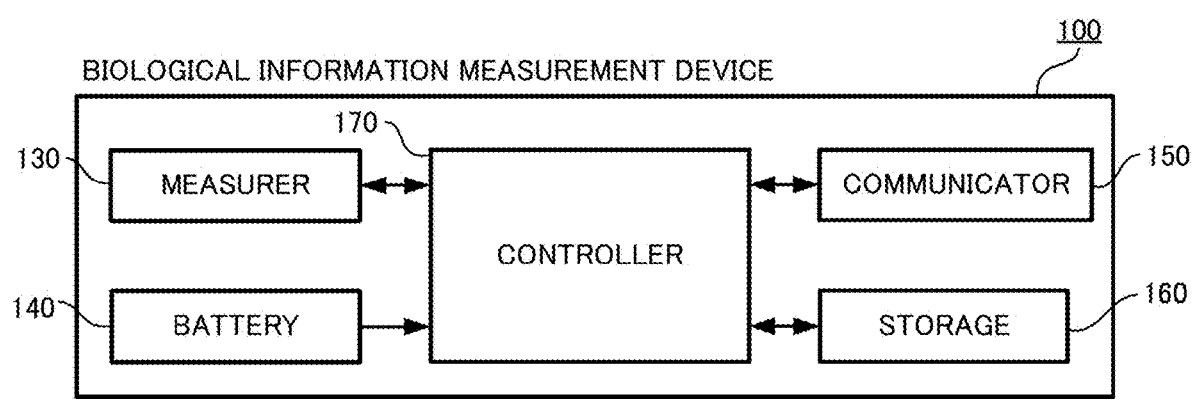
FIG. 9 is a block diagram illustrating a configuration of the biological information measurement device according to the embodiment of the present disclosure.

FIG. 9 is a block diagram illustrating a hardware configuration of the biological information measurement device 100. The biological information measurement device 100 includes a measurer 130, a battery 140, a communicator 150, a storage 160, and a controller 170. The respective constituent units of the biological information measurement device 100 are interconnected by an internal bus.

The measurer 130 acquires volume pulse wave data, based on an instruction from the controller 170 and outputs the acquired volume pulse wave data to the controller 170. The measurer 130, for example, includes the pulse wave sensor 120, which measures a volume pulse wave at a measurement target site.

The battery 140 supplies power necessary for the respective constituent units of the biological information measurement device 100 to operate.

The communicator 150 is an interface that can be connected to a communication network, such as the Internet. The communicator 150 communicates with a communicator of the analysis device 200, an external terminal, a server, a memory, or the like via the communication network. The communicator 150 includes, for example, a communication antenna through which the communicator 150 transmits volume pulse wave data to the analysis device 200.

The storage 160 includes a random access memory (RAM), a read only memory (ROM), a flash memory, and the like. The storage 160 stores programs that are executed by the controller 170 and various types of data. The storage 160 also functions as a working memory for the controller 170 to perform processing.

The storage 160 stores volume pulse wave data measured by the pulse wave sensor 120, in association with identification information (for example, a user identification (ID)) of a subject and information on acquisition date and time of the data.

The controller 170 includes a central processing unit (CPU) or the like and performs control of the respective constituent units of the analysis device 200. The controller 170 performs volume pulse wave data transfer processing in FIG. 12 by executing a program stored in the storage 160.

The controller 170 acquires volume pulse wave data from the measurer 130 with a predetermined sampling period and makes the storage 160 store the acquired volume pulse wave data in association with the identification information of the subject and the information on acquisition date and time of the data. The controller 170 also controls the communicator 150 to transmit the volume pulse wave data to the analysis device 200 in conjunction with identification information of a user and the information on acquisition date and time of the data. The above is the configuration of the biological information measurement device 100.

Figure 10:
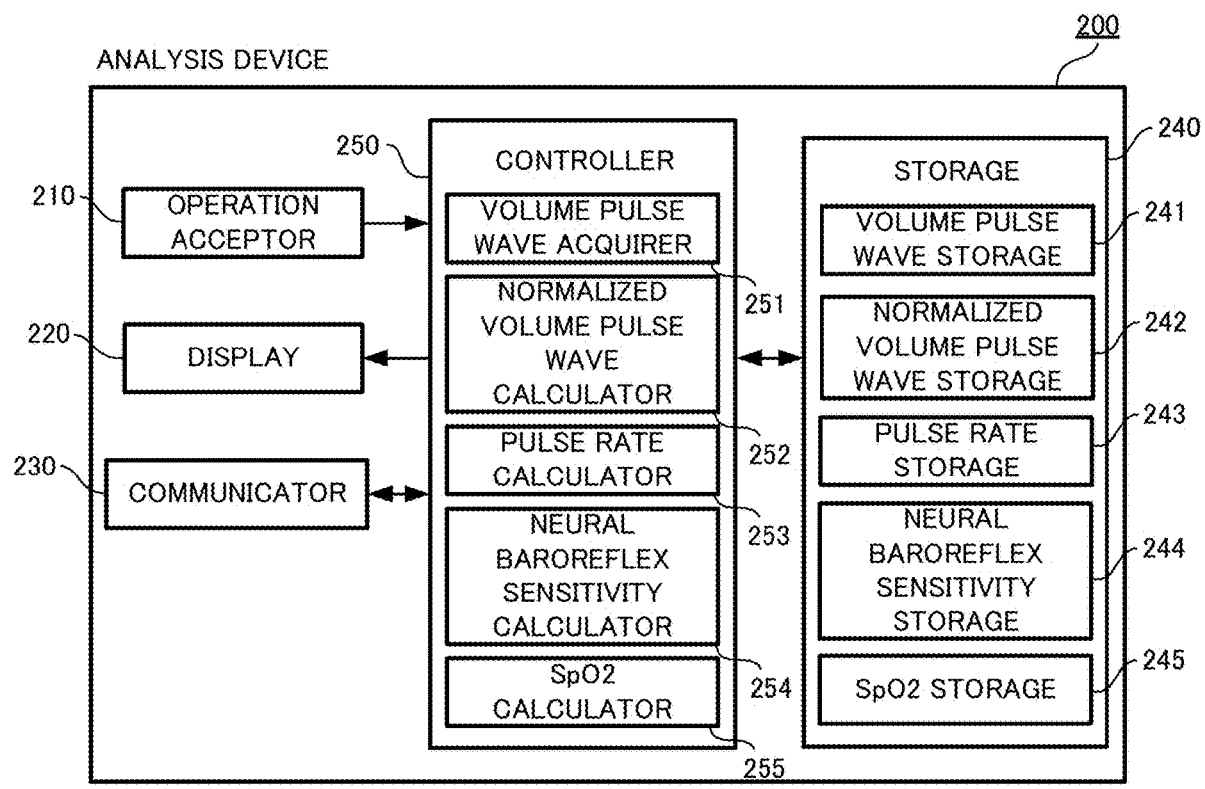
FIG. 10 is a block diagram illustrating a configuration of an analysis device according to the embodiment of the present disclosure.

FIG. 10 is a block diagram illustrating a hardware configuration of the analysis device 200. The analysis device 200 is, for example, a general-purpose computer.

The analysis device 200 includes an operation acceptor 210, a display 220, a communicator 230, a storage 240, and a controller 250. The respective constituent units of the analysis device 200 are interconnected via an internal bus (not illustrated).

The operation acceptor 210 accepts an instruction from a user and supplies the controller 250 with an operation signal corresponding to the accepted instruction. The operation acceptor 210 includes, for example, a keyboard and a mouse. The operation acceptor 210 accepts, for example, an instruction relating to a condition for pulse wave measurement performed by the biological information measurement device 100 (such as an instruction relating to the start or end of pulse wave measurement and an instruction relating to a sampling period).

The display 220 displays various types of images to the user, based on image data supplied from the controller 250. The display 220 includes, for example, a liquid crystal panel or an organic electro luminescence (EL) panel.

The communicator 230 is an interface that can be connected to a communication network, such as the Internet. The communicator 230 communicates with the communicator 150 of the biological information measurement device 100, an external terminal, a server, a memory, or the like via the communication network.

The storage 240 includes a RAM, a ROM, a flash memory, a hard disk device, and the like. The storage 240 stores programs that are executed by the controller 250 and various types of data. The storage 240 also functions as a working memory for the controller 250 to perform processing. The storage 240 further includes a volume pulse wave storage 241, a normalized volume pulse wave storage 242, a pulse rate storage 243, a neural baroreflex sensitivity storage 244, and an SpO2 storage 245.

The volume pulse wave storage 241 stores a volume pulse wave measured by the biological information measurement device 100, in association with the identification information of the subject and the information on acquisition date and time of the data.

The normalized volume pulse wave storage 242 stores a photoelectric normalized volume pulse wave (normalized pulse volume (NPV)) calculated based on a volume pulse wave measured by the biological information measurement device 100, in association with the identification information of the subject and the information on acquisition date and time of the data.

A normalized pulse volume is expressed by the following formula. Note, however, that PGac denotes a plethysmogram AC component. PGdc denotes a plethysmogram DC component. PGdc is calculated based on a mean value over a pulsation period of the amount of transmitted light, which is calculated by subtracting the amount of light absorbed by a living tissue from the amount of light radiated on the living tissue.

$$NPV = PGac/PGdc \quad (2)$$

Figure 11:
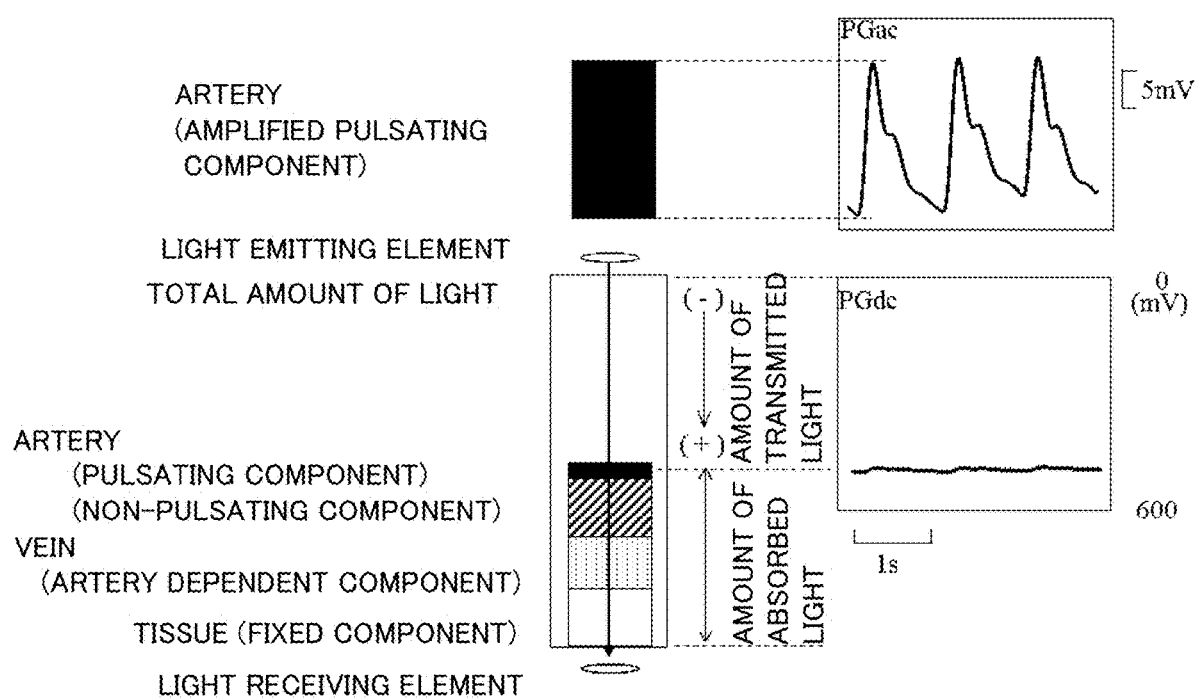
FIG. 11 is a diagram for a description of a situation in which light radiated from a light emitting element is absorbed by a living tissue.

FIG. 11 is a diagram for a description of the plethysmogram AC component PGac and the plethysmogram DC component PGdc. As illustrated in FIG. 11, the amount of light absorbed by a living tissue (the amount of absorbed light) is composed of a non-pulsation component that is absorbed regardless of pulsation of arteries, a pulsation component that is absorbed when the arteries pulsate, a vein dependent component that is absorbed by veins, and a tissue component that is absorbed by the tissue. Since there are individual differences in tissue components, influenced by differences in physical builds and the like, the ratio of the pulsation component to the amount of absorbed light changes when the ratio of the tissue component changes, as a result of which influence of the individual differences is also reflected on a pulse volume PV.

On the other hand, since the normalized pulse volume is a ratio of a plethysmogram DC component to a plethysmogram AC component and is a non-dimensional absolute amount, the normalized pulse volume is never influenced by differences in tissue components. Thus, numerical values of normalized pulse volumes can be compared with each other even when subjects, measurement date and time, measurement conditions, or the like are different from each other.

Returning to FIG. 10, the pulse rate storage 243 stores pulse rate data calculated based on a volume pulse wave measured by the biological information measurement device 100, in association with the identification information of the subject and the information on acquisition date and time of the data. The pulse rate is, for example, the number of pulsations per minute of an artery.

The neural baroreflex sensitivity storage 244 stores neural baroreflex sensitivity calculated based on a volume pulse wave measured by the biological information measurement device 100, in association with the identification information of the subject and the information on acquisition date and time of the data. The neural baroreflex sensitivity is a slope of a regression line that indicates a correlation between normalized pulse volumes and pulse intervals in a baroreflex series that is not influenced by the sympathetic nervous system and is an index that indicates a state of a neural baroreflex function.

The SpO2 storage 245 stores SpO2 calculated based on a volume pulse wave measured by the biological information measurement device 100, in association with the identification information of the subject and the information on acquisition date and time of the data. SpO2 indicates a saturation degree of oxygen contained in the arterial blood.

The controller 250 includes a CPU or the like and performs control of the respective constituent units of the analysis device 200. The controller 250 performs analysis processing in FIG. 13 by executing a program stored in the storage 240.

The controller 250, from a functional perspective, includes a volume pulse wave acquirer 251, a normalized volume pulse wave calculator 252, a pulse rate calculator 253, a neural baroreflex sensitivity calculator 254, and an SpO2 calculator 255.

The volume pulse wave acquirer 251 acquires a volume pulse wave from the biological information measurement device 100 and registers the acquired volume pulse wave in the pulse volume storage 241.

The normalized volume pulse wave calculator 252 calculates a normalized volume pulse wave, based on a volume pulse wave acquired by the volume pulse wave acquirer 251 and registers the normalized volume pulse wave in the normalized volume pulse wave storage 242. More specifically, the normalized volume pulse wave calculator 252 calculates a normalized volume pulse wave (normalized pulse volume) by dividing amplitude of the plethysmogram AC component PGac by a mean value of the plethysmogram DC component PGdc with respect to each arterial pulse, based on a volume pulse wave acquired by the volume pulse wave acquirer 251.

The pulse rate calculator 253 acquires intervals between pulses (inter-beat intervals) corresponding to volume pulse wave data in a time series, calculates a pulse rate per unit time, based on the acquired inter-beat intervals, and registers the calculated pulse rate per unit time in the pulse rate storage 243.

The neural baroreflex sensitivity calculator 254 detects a baroreflex series in a blood vessel that is not influenced by the sympathetic nervous system, based on a normalized volume pulse wave calculated by the normalized volume pulse wave calculator 252 and inter-beat intervals acquired by the pulse rate calculator 253 and calculates neural baroreflex sensitivity values in the baroreflex series. The neural baroreflex sensitivity calculator 254 also registers the calculated neural baroreflex sensitivity values in the neural baroreflex sensitivity storage 244.

The SpO2 calculator 255 calculates SpO2 values, based on an acquired volume pulse wave. More specifically, the SpO2 calculator 255 calculates SpO2 values by calculating ratios between the amount of reduced hemoglobin, which is hemoglobin not bound to oxygen, and the amount of oxyhemoglobin, which is hemoglobin bound to oxygen, in the blood, using differences between absorptivities of infrared rays or red light that are absorbed by the arterial blood. The SpO2 calculator 255 also registers the calculated SpO2 values in the SpO2 storage 245. The above is the configuration of the analysis device 200.

Next, a measurement method of biological information that is performed using the biological information measurement system 1 will be described.

First, a user attaches the biological information measurement device 100 on one of the auricles of a subject. More specifically, the user presses the first member 111 and second member 112 of the clip 110 apart against an elastic force of the spring, using fingers and widens distance between the tip end portion 111B of the first member 111 and the tip end portion 112D of the second member 112. Next, the user arranges the clip 110 in such a manner that the first member 111 and the second member 112 sandwich the scapha of the auricle from both sides.

Next, the user attaches the biological information measurement device 100 on the auricle of the subject as illustrated in FIG. 7 by closing the first member 111 and the second member 112. On this occasion, since the biological information measurement device 100 is configured as described above, the pulse wave sensor 120 is arranged in such a way as to measure a volume pulse wave in the artery of the helix, which is not influenced by compression to the scapha by the first member 111 and the second member 112.

Next, the user operates the operation acceptor 210 and instructs a start date and time and end date and time of measurement of a volume pulse wave. Upon acceptance of an operation signal from the operation acceptor 210, the analysis device 200 transmits information on the start date and time and end date and time of measurement of a volume pulse wave to the biological information measurement device 100. When the communicator 150 of the biological information measurement device 100 accepts the information from the analysis device 200, the biological information measurement device 100 performs the volume pulse wave data transfer processing in FIG. 12.

(Volume Pulse Wave Data Transfer Processing)

Figure 12:
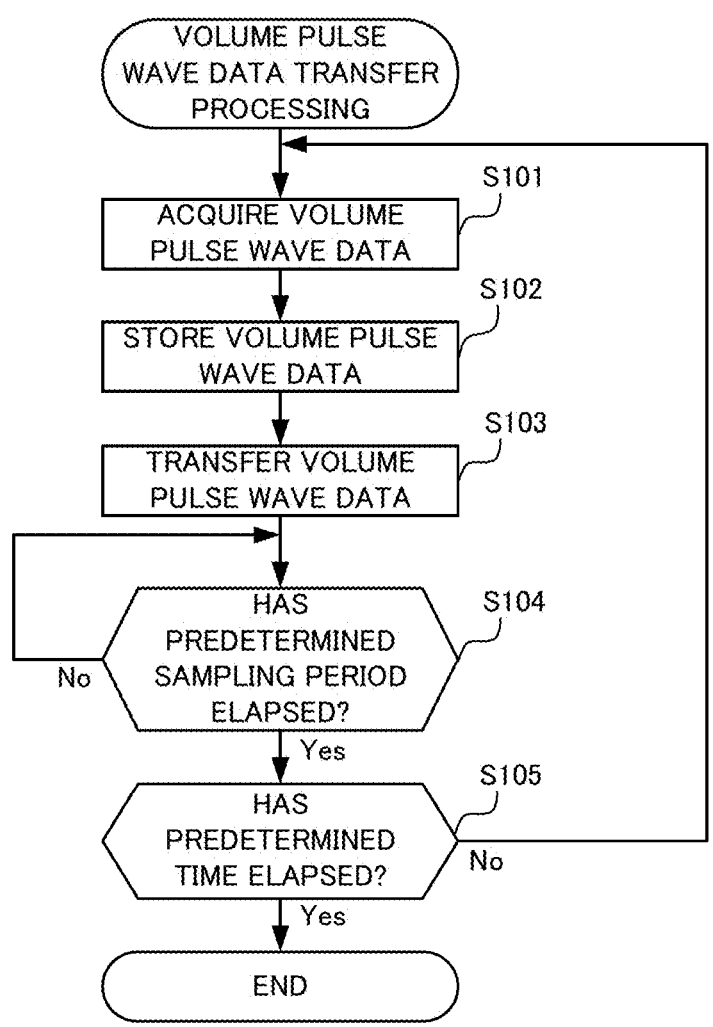
FIG. 12 is a flowchart illustrating a flow of volume pulse wave data transfer processing.

With reference to FIG. 12, the volume pulse wave data transfer processing, which the biological information measurement device 100 performs when being instructed to measure a volume pulse wave by the analysis device 200, will be described below. The volume pulse wave data transfer processing is processing of acquiring volume pulse wave data from a measurement target site and transmitting the acquired volume pulse wave data to the analysis device 200.

First, the controller 170 acquires a piece of volume pulse wave data from a signal that the pulse wave sensor 120 has detected (step S101). More specifically, the controller 170 makes the light emitting element 121 emit radiated light with a predetermined sampling period, makes the pulse wave sensor 120 measure a volume pulse wave in an artery by making the light receiving element 122 receive transmitted light that is transmitted through the measurement target site of the auricle, and thereby acquires a piece of volume pulse wave data.

Next, the controller 170 makes the storage 160 store the piece of volume pulse wave data acquired in step S101, in association with identification information and data acquisition date and time (step S102).

Next, the controller 170 transfers the piece of volume pulse wave data acquired in step S101 to the analysis device 200 in association with the identification information and the data acquisition date and time (step S103). Upon acquisition of the volume pulse wave data from the biological information measurement device 100, the analysis device 200 performs analysis processing in FIG. 13.

Note that the piece of volume pulse wave data stored in the storage 160 may be deleted from the storage 160 after a lapse of a certain period since the transfer to the analysis device 200.

Next, the controller 170 determines whether or not the predetermined sampling period has elapsed since the processing in step S101 (step S104). When the predetermined sampling period has elapsed (step S104; Yes), the process proceeds to step S105. On the other hand, when the predetermined sampling period has not elapsed (step S104; No), the process stands by until the predetermined sampling period has elapsed.

Next, the controller 170 determines whether or not a predetermined time has elapsed since the start date and time of measurement (step S105). The predetermined time is set based on the start date and time and end date and time of measurement. When the predetermined time has elapsed (step S105; Yes), the process is terminated. On the other hand, when the predetermined time has not elapsed (step S105; No), the process returns to the processing in step S101. The above is the flow of the volume pulse wave data transfer processing.

(Analysis Processing)

Figure 13:
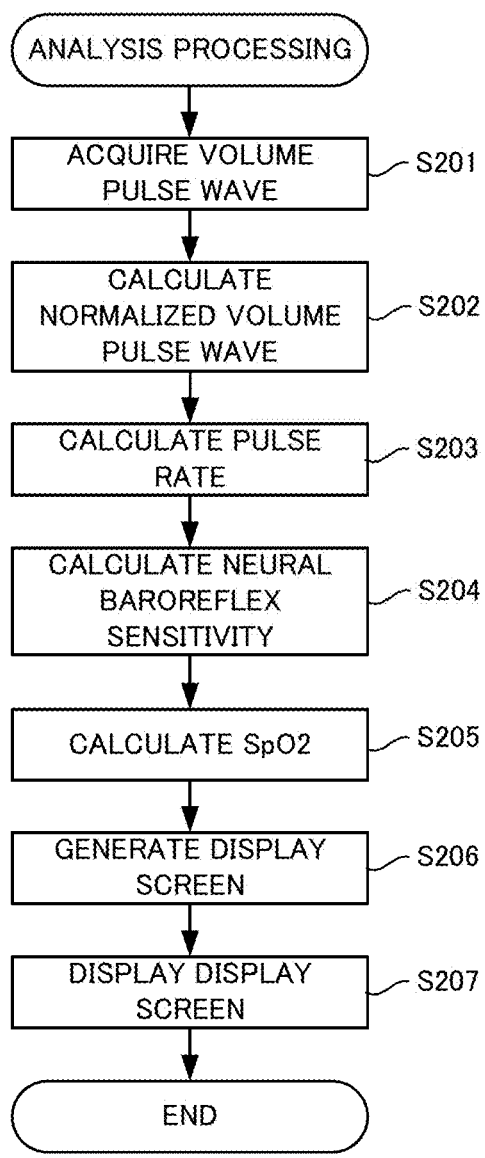
FIG. 13 is a flowchart illustrating a flow of analysis processing.

With reference to FIG. 13, the analysis processing, which the analysis device 200 performs when the analysis device 200 receives volume pulse wave data from the biological information measurement device 100, will be described below. The analysis processing is processing of calculating various types of data, based on volume pulse wave data.

First, the volume pulse wave acquirer 251 makes the communicator 230 receive a volume pulse wave that is transmitted from the communicator 150 of the biological information measurement device 100, thereby acquiring volume pulse wave data and registers the acquired volume pulse wave data in the volume pulse wave storage 241 (step S201).

Next, the normalized volume pulse wave calculator 252 calculates a normalized volume pulse wave, based on the volume pulse wave acquired in step S201 and registers the calculated normalized volume pulse wave in the normalized volume pulse wave storage 242 (step S202).

Next, the pulse rate calculator 253 acquires inter-beat intervals, based on the volume pulse wave acquired in step S201, calculates a pulse rate, based on the acquired inter-beat intervals, and registers the calculated pulse rate in the pulse rate storage 243 (step S203).

Next, the neural baroreflex sensitivity calculator 254 calculates neural baroreflex sensitivity values, based on the normalized volume pulse wave calculated in step S202 and the inter-beat intervals acquired in step S203 and registers the calculated neural baroreflex sensitivity values in the neural baroreflex sensitivity storage 244 (step S204).

Next, the SpO2 calculator 255 calculates SpO2 values, based on the volume pulse wave acquired in step S201 and registers the calculated SpO2 values in the SpO2 storage 245 (step S205).

Next, the controller 250 generates a display screen that displays the volume pulse wave acquired in step S201 and various types of data calculated in steps S202 to S205 in a list form (step S206).

Figure 14:
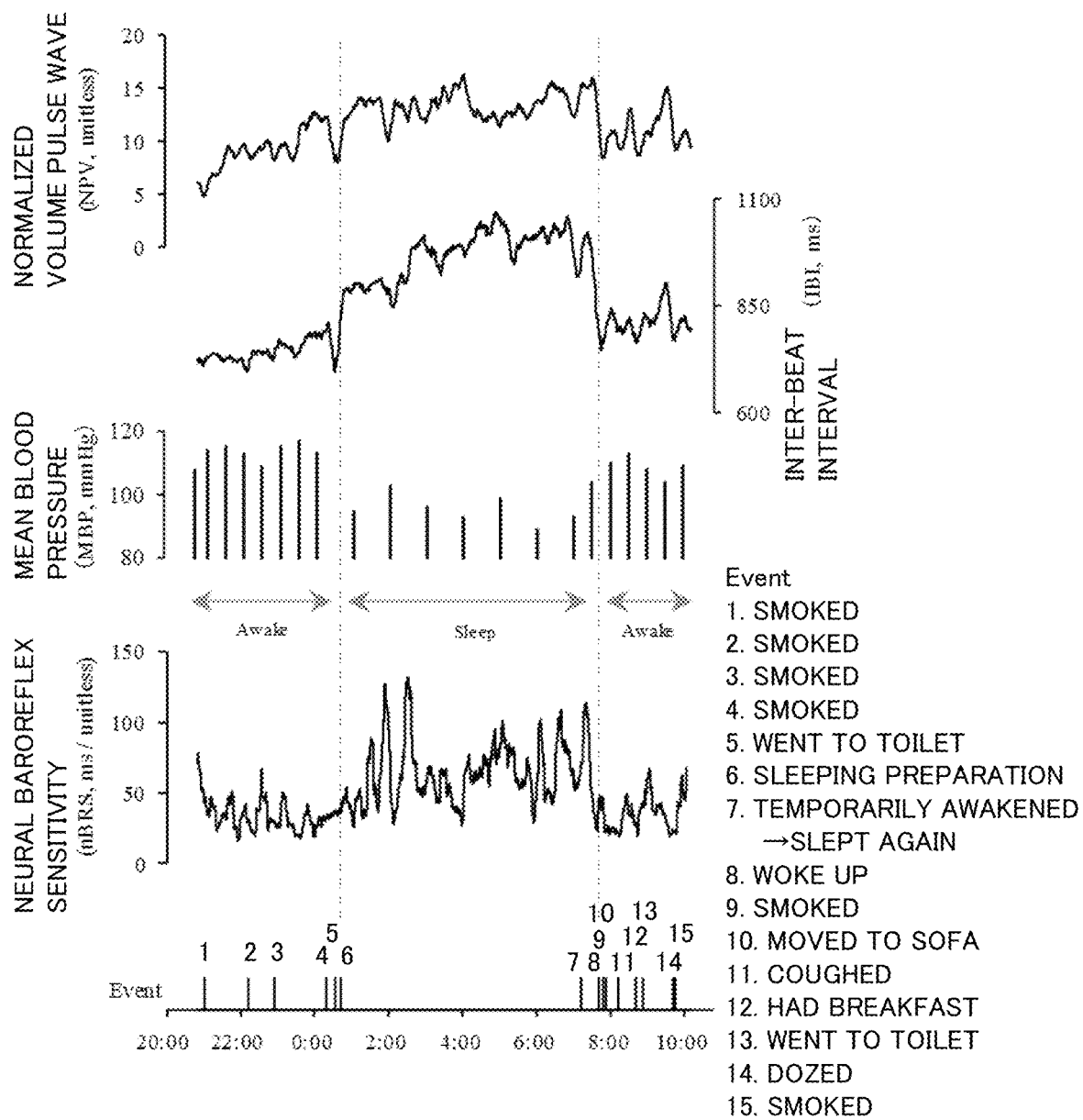
FIG. 14 is a diagram illustrating an example of a display screen.

FIG. 14 is an example of a display screen that displays various types of data in a list form. The display screen displays mean blood pressure MBP in a waveform and, in conjunction therewith, displays a calculated normalized volume pulse wave (normalized pulse volume NPV), inter-beat intervals IBI, and neural baroreflex sensitivity nBRS in waveforms. The chart named Event in FIG. 14 indicates behavioral events of the subject the descriptions and occurrence times of which the subject himself/herself recorded and are registered in the analysis device 200 and displayed on the display screen. Information relating to the chart Event is, for example, input to a communication terminal of the subject by the subject and transmitted from the communication terminal of the subject to the analysis device 200. The numeral of each item in the chart Event indicates a description and occurrence time of a specific behavioral event of the subject. For example, the item 1 in the chart Event indicates that the subject smoked approximately at 21:00. Note that FIG. 14 is illustrated with display of a pulse rate and SpO2 values omitted.

Next, the controller 250 makes the display 220 display the display screen generated in step S206 (step S207) and terminates the process. The above is the flow of the analysis processing that the analysis device 200 performs.

After completion of the volume pulse wave measurement, the user removes the clip 110 from the helix by pressing apart the first member 111 and the second member 112. When all the steps described above have been processed, the pulse wave measurement using the biological information measurement system 1 is finished.

Since the biological information measurement device 100 is configured to be attachable on one of the auricles of a subject as described above, the biological information measurement system 1 can be used for the following uses. Regarding, for example, a heart disease event, disease incidence does not decrease as expected even when risk factors (for example, an LDL cholesterol level) are controlled, and, in addition, it is difficult to predict an occurrence time of such an event. Thus, attaching the biological information measurement device 100 on one of the auricles of a subject constantly and making the biological information measurement device 100 measure volume pulse wave data enables an occurrence of a heart disease event to be monitored 24 hours a day.

When a previous state that causes a heart disease event can be specified, it is possible to achieve prediction of the heart disease event. Thus, acquiring volume pulse wave data from a large number of subjects wearing the biological information measurement devices 100 and analyzing an overall tendency of the volume pulse wave data also enables a previous state causing a heart disease event to be specified.

EXAMPLE

Next, with reference to FIGS. 15A, 15B, and 16, a verification experiment for evaluating usefulness of the biological information measurement device and a result of the verification experiment will be described. In this experiment, a biological information measurement device that is capable of measuring a volume pulse wave in the artery (STA) of the helix of one of the auricles with a sensor when the scapha of the auricle is clamped by a clip was produced and used. The biological information measurement device was configured such that the inclination of the sensor with respect to the clip can be changed to a predetermined sensor angle.

Figure 15A:
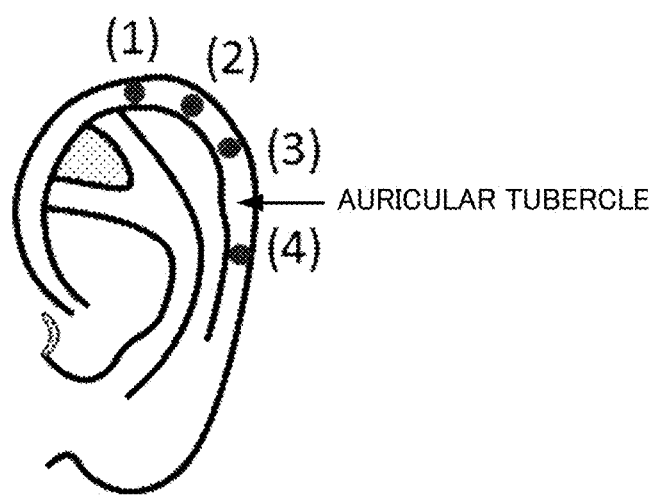
FIG. 15A is a diagram illustrating a pattern of sensor positions in Example.
Figure 15B:
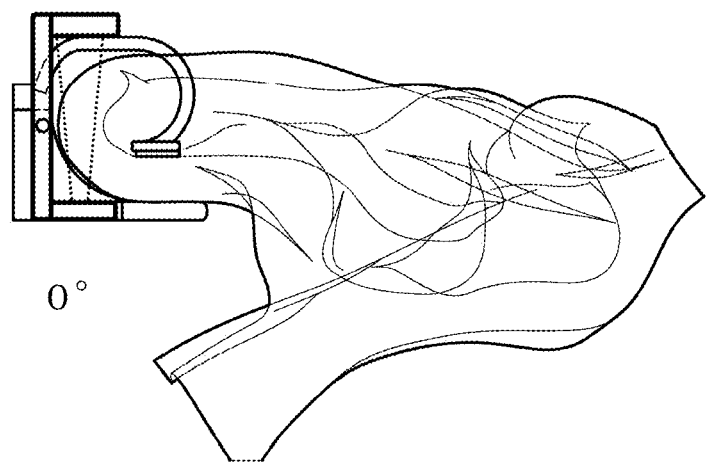
FIG. 15B is a diagram illustrating a pattern of sensor angles in Example.
Figure 15B:
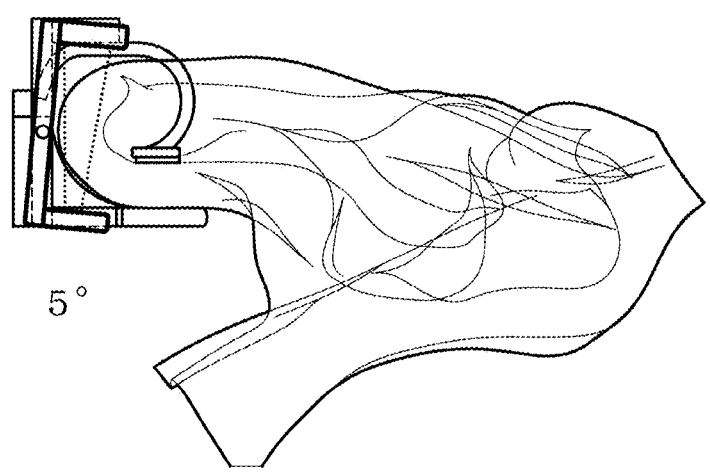
Figure 15B:
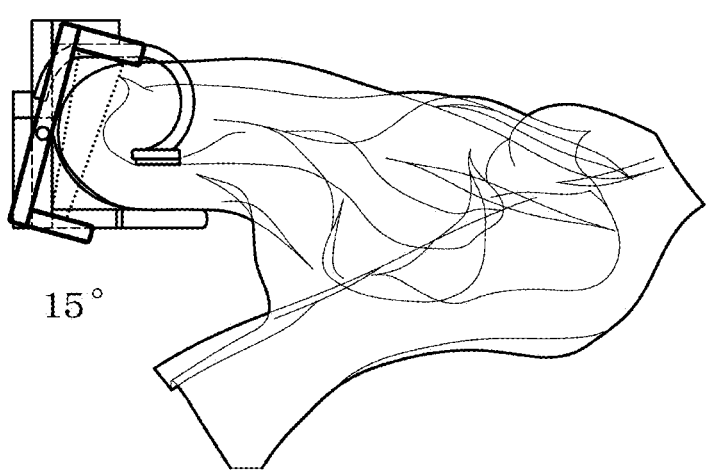

FIGS. 15A and 15B are diagrams illustrating a pattern of sensor positions and a pattern of sensor angles, respectively, in the example. In this experiment, volume pulse waves in the artery when the biological information measurement device is attached on respective sensor positions 1 to 4 on the helix illustrated in FIG. 15A were measured. In addition, changes in the volume pulse waves when the sensor angle is changed to 0°, 5°, and 15° as illustrated in FIG. 15B were examined.

The sensor angle is specified by the direction of light radiated from the sensor when the biological information measurement device is attached on the auricle. When the sensor angle is set at 0°, the direction of light radiated from the sensor is vertical to the first member 111. When the sensor angle is set at 5°, the direction of light radiated from the sensor is a direction inclined from the vertical direction to the external auditory meatus side by 5° with respect to the first member 111. In this experiment, volume pulse waves were measured with 37 subjects as targets when the biological information measurement device was attached at the sensor positions 1 to 4 and the sensor angle was set at 0°, 5°, and 15°, and statistical processing was applied to measurement results.

Figure 16:
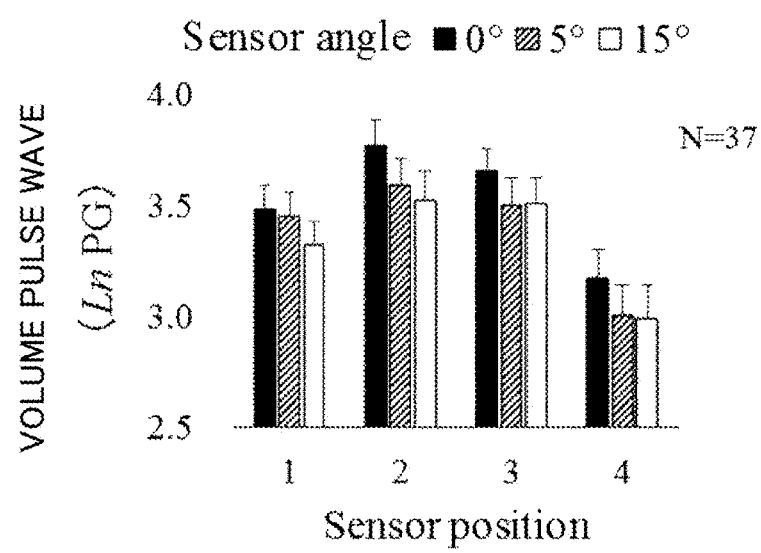
FIG. 16 is a graph illustrating experimental results in Example.

FIG. 16 is a graph illustrating experimental results in the example. The ordinate and abscissa of FIG. 16 represent the natural logarithms LnPG of volume pulse waves (plethysmograms) and the respective sensor positions 1 to 4, respectively. In addition, results of measurement of volume pulse waves when the sensor angle is set at 0°, 5°, and 15° are illustrated with respect to each of the sensor positions 1 to 4. As illustrated in FIG. 16, although volume pulse waves in the case of the sensor position 4 were measured to be lower than the cases of the sensor positions 1 to 3, volume pulse waves that are substantially equal to one another were able to be measured in the cases of the sensor positions 1 to 3. Thus, it can be understood that it is possible to measure volume pulse waves that are comparable with one another, at any portion of the helix as long as the portion is located at a position on the auricle above the auricular tubercle.

It can also be seen that, at any of the respective sensor positions 1 to 4, the numerical values of volume pulse waves measured by the biological information measurement device do not change substantially even when the sensor angle of the biological information measurement device changes. Thus, it can be understood that the biological information measurement device 100 is capable of measuring a volume pulse wave with high precision even when the sensor angle changes. Therefore, it can be understood that it is possible to measure volume pulse waves that are comparable with one another, at any portion of the helix as long as the portion is located at a position on the auricle above the auricular tubercle, regardless of at whatever angle the biological information measurement device is attached. The above is the explanation of the verification experiment for evaluating usefulness of the biological information measurement device and a result of the verification experiment.

As described thus far, the biological information measurement device 100 according to the embodiment includes the clip 110 that is attachable on a portion of a living body and the pulse wave sensor 120 that is disposed on the clip 110 and that measures a volume pulse wave at a measurement target site that is different from an attachment target site at which the biological information measurement device 100 is attached with the clip 110. This configuration enables not only a volume pulse wave to be measured accurately but also a wearable device with high usability to be achieved.

In addition, the biological information measurement device 100 according to the embodiment includes the pulse wave sensor 120 that is configured to be capable of measuring a volume pulse wave in an artery running inside the helix of one of the auricles when the scapha of the auricle is clamped from both sides by the clip 110. Thus, measuring a volume pulse wave in the artery running inside the helix that is not compressed even when the scapha is clamped from both sides enables the volume pulse wave to be measured with higher accuracy.

Further, differing from the biological information measurement device of Patent Literature 1 that is attached on the lobule of ear, which moves up and down when the subject moves his/her mouth, the biological information measurement device 100 according to the embodiment is configured such as to measure a volume pulse wave in the artery running inside the helix that is unlikely to be influenced by a body motion. Thus, it is possible to measure a volume pulse wave accurately even when the subject performs conversation or the like in daily life.

Without being limited to the above embodiment, the present disclosure may be embodied in variations to be described below.

(Variations)

Although, in the above-described embodiment, one of the auricles was used as a target site for detection of volume pulse wave data, the present disclosure is not limited to the configuration. Any site may be used as long as the site is a site at which a pulse wave in an artery can be detected. For example, an inner ear, a wrist, a finger, an arm, a neck, a head, a foot, or the like may be used. In a situation where body motion is negligible, for example, the lobule of ear may be used as a target site for detection of volume pulse wave data.

Although, in the above-described embodiment, the clip 110 was used as attachment means, the present disclosure is not limited to the configuration. As the attachment means, for example, earphones, earrings, eyeglasses, sunglasses, a bracelet, a band, a string, a finger ring, or a ring may be used. A desirable ornament (accessory) may be applied to the attachment means.

Although, in the above-described embodiment, the cushion 111C was disposed on the tip end portion 111B of the first member 111, the present disclosure is not limited to the configuration. For example, an elastic member, such as a cushion, may be disposed on the tip end portion 112D of the second member 112, or elastic members may be disposed on both the tip end portion 111B and the tip end portion 112D. The cushion 111C is not an indispensable component, and the biological information measurement device 100 may be used with the cushion 111C removed from the tip end portion 111B.

Although, in the above-described embodiment, the first member 111 and the second member 112 were configured to be openable and closable via the rotation shaft 113, the present disclosure is not limited to the configuration. For example, the tip end portion of the first member 111 and the tip end portion of the second member 112 may be configured to be openable and closable by connecting the base end portion of the first member 111 and the base end portion of the second member 112 to each other, thereby integrally forming the first member 111 and the second member 112 and forming the first member 111 and the second member 112, using an elastically deformable material. Alternatively, the first member 111 may be formed using an elastically deformable material, and the second member 112 may be formed using a material more rigid than the first member 111 lest the positional relationship between the first sensor support portion 112B and the second sensor support portion 112C is shifted.

Although, in the above-described embodiment, normalized volume pulse wave data and the like were calculated and displayed on the display 220 after reception of volume pulse wave data had been finished, the present disclosure is not limited to the configuration. For example, the communicator 150 may be made to collectively transmit volume pulse wave data every fixed period, the communicator 230 may be made to receive volume pulse wave data, the controller 250 may be made to calculate various types of data in real time, based on the received volume pulse wave data, and a display screen displayed on the display 220 may be updated every fixed period.

Although, in the above-described embodiment, volume pulse wave data were used as pulse wave data, the present disclosure is not limited to the configuration. For example, pressure pulse wave data may be used as pulse wave data.

Although, in the above-described embodiment, a transmission-type photoelectric pulse wave sensor was used as the pulse wave sensor 120, the present disclosure is not limited to the configuration. For example, a reflection-type photoelectric pulse wave sensor that measures a volume pulse wave by irradiating a living body with infrared rays, red light, or the like and measuring reflected light that is reflected inside the living body may be used. Note that, when a volume pulse wave is measured using a reflection-type photoelectric pulse wave sensor, measured data cannot be compared between individuals and it is difficult to calculate SpO2 or the like because no method for correcting scattering of light, which has individual differences, has been established. Thus, it is preferable to measure a photo-plethysmogram, using a transmission-type photoelectric pulse wave sensor.

Although, in the above-described embodiment, the pulse wave sensor 120 that measures a pulse wave was used as measurement means, the present disclosure is not limited to the configuration. Without being limited to measurement means that measures a pulse wave, any measurement means may be used as long as the measurement means is measurement means that measures biological information. For example, the measurement means may be a sensor that measures blood pressure, cardiac sound, or electrocardiograph. In addition to the measurement means that measures biological information, measurement means, such as a global positioning system (GPS) sensor and an acceleration sensor, may be used.

Although, in the above-described embodiment, a pulse rate, neural baroreflex sensitivity values, and SpO2 values were calculated based on a volume pulse wave, the present disclosure is not limited to the configuration. For example, a vascular age, a stress level, or the like represented by a numerical value may be calculated based on a volume pulse wave.

Although, in the above-described embodiment, the biological information measurement device 100 and the analysis device 200 are separate devices, the present disclosure is not limited to the configuration. For example, the biological information measurement device 100 and the analysis device 200 may be integrally configured. The biological information measurement device 100 and the communication antenna may be configured as separate bodies, and power necessary for operation of the biological information measurement device 100 may be supplied from a power supply (battery) that is a separate body from the biological information measurement device 100. In this case, it may be configured such that an input/output interface (I/F) that can be connected to a cable is disposed in the biological information measurement device 100 and the biological information measurement device 100 and the communication antenna or the power supply are electrically connected to each other via the cable.

Although, in the above-described embodiment, the Operation acceptor 210 and the display 220 were configured as separate bodies, the present disclosure is not limited to the configuration. For example, the Operation acceptor 210 and the display 220 may be integrally configured by a touch panel. The touch panel is only required to display an operation screen that accepts predetermined operations and, in conjunction therewith, supply the controller 250 with an operation signal corresponding to a position at which the user performs a touch operation in the operation screen.

Although, in the above-described embodiment, volume pulse wave data measured by the pulse wave sensor 120 were stored in the storage 160 in association with information on acquisition date and time of the data, the present disclosure is not limited to the configuration. For example, volume pulse wave data measured by the pulse wave sensor 120 may be transferred to the analysis device 200 and subsequently be stored in the storage 240 in association with information on acquisition date and time of the data.

Although, in the above-described embodiment, volume pulse wave data measured by the pulse wave sensor 120 were directly used in the analysis processing, the present disclosure is not limited to the configuration. For example, filter processing may be performed on volume pulse wave data before or during the performance of the analysis processing, or correction of volume pulse wave data may be performed based on information from an acceleration sensor or the like.

Although, in the above-described embodiment, various types of data, such as normalized volume pulse wave data, were stored in the storage 240 of the analysis device 200, the present disclosure is not limited to the configuration. For example, the whole or a part of various types of data may be stored in an external server, computer, or the like via the communication network.

Although, in the above-described embodiment, the Internet was used as the communication network, the present disclosure is not limited to the configuration. For example, the communication network may be achieved using a local area network (LAN), a dedicated line, or the like.

Although, in the above-described embodiment, the analysis device 200 operated based on a program stored in the storage 240, the present disclosure is not limited to the configuration. For example, a functional configuration that is achieved by the program may be achieved by hardware.

Although, in the above-described embodiment, the analysis device 200 was a general-purpose computer, such as a personal computer, the present disclosure is not limited to the configuration. For example, the analysis device 200 may be achieved by a dedicated system or may be a computer running on a cloud. Although the processing that the analysis device 200 performs were achieved by a device with the above-described physical configuration executing a program stored in the storage 240, the present disclosure may be achieved as a program or may be achieved as a storage medium recording the program.

A device that performs the above-described processing operation may be configured by storing a program causing the above-described processing operation to be performed, in a computer-readable recording medium, such as a flexible disk, a compact disk read-only memory (CD-ROM), a digital versatile disk (DVD), and a magneto-optical disk (MO), distributing the recording medium, and installing the program in a computer.

Although, in the above-described embodiment, the biological information measurement device 100 was attached on a human body, the present disclosure is not limited to the configuration. The biological information measurement device 100 may be configured to be attachable on an animal other than human.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2018-64067, filed on Mar. 29, 2018, the entire disclosure of which is incorporated by reference herein.

INDUSTRIAL APPLICABILITY

The biological information measurement device of the present disclosure is useful because the biological information measurement device is capable of measuring biological information accurately even when the biological information measurement device is attached on a living body.

REFERENCE SIGNS LIST

1 Biological information measurement system
100 Biological information measurement device
110 Clip
111 First member
111A Base end portion
111B Tip end portion
111C Cushion
111D Space
112 Second member
112A Base end portion
112B First sensor support portion
112C Second sensor support portion
112D Tip end portion
112E Slit
112F, 112G Auricle contact portion
113 Rotation shaft
120 Pulse wave sensor
121 Light emitting element
122 Light receiving element
130 Measurer
140 Battery
150, 230 Communicator
160, 240 Storage
170, 250 Controller
200 Analysis device
210 Operation acceptor
220 Display
241 Volume pulse wave storage
242 Normalized volume pulse wave storage
243 Pulse rate storage
244 Neural baroreflex sensitivity storage
245 SpO2 storage
251 Volume pulse wave acquirer
252 Normalized volume pulse wave calculator
253 Pulse rate calculator
254 Neural baroreflex sensitivity calculator
255 SpO2 calculator

The invention claimed is:

1. A biological information measurement device comprising:
a first member comprising a base end portion including a space formed at a central portion;
a second member comprising a base end portion, including a first sensor support portion and a second sensor support portion, wherein the first sensor support portion and the second sensor support portion are respective end portions of the base end portion of the second member and extend perpendicularly from the base end portion of the second member, wherein the first member is joined to the second member in a rotatable manner; and
a measurement means disposed on a portion of the second member, arranged in such a way as not to compress a helix of an auricle when the second member is configured to be attached on a scapha of the auricle, and measuring biological information of an artery running in the helix;
wherein the first member and the second member are connected to each other at base end portions of the first member and the second member, and are configured to clamp the scapha of the auricle from both sides.

2. The biological information measurement device according to claim 1, wherein
the measurement means includes a non-contact type sensor that measures the biological information, using transmitted light, and
the first and second members are in such a way that the measurement means does not come into contact with the helix of the auricle when the first and second members are attached in such a way as to clamp the scapha of the auricle from both sides.

3. The biological information measurement device according to claim 1, wherein
the measurement means includes a pulse wave sensor that measures a pulse wave in the artery running in the helix.

4. The biological information measurement device according to claim 1, wherein the first and second members comprise clip that is configured to be attached in such a way that tip end portions of the clip clamp the scapha of the auricle from both sides, and the measurement means is disposed further on a base end side than a tip end side of the clip and measures the biological information in the artery running in the helix.

5. The biological information measurement device according to claim 1, wherein the base end portion of the first member and a tip end portion of the first member are collectively shaped into an L-shape.

6. The biological measurement device according to claim 1, wherein the first sensor support portion of the second member in the space formed at the central portion results in the first member not being prevented from rotating with respect to the second member.

7. A biological information measurement device comprising:
  a first member and a second member configured to be attached on a scapha of an auricle in such a way as to clamp the scapha from both sides; and
  a measurement means disposed on a portion of the second member, arranged in such a way as not to compress a helix of the auricle when the second member is attached on the scapha of the auricle, and measuring biological information of an artery running in the helix, wherein
  the first member and the second member are connected to each other at base end portions of the first member and the second member, wherein the second member includes first and second support member portions that extend perpendicularly from respective end portions of the base end portion of the second member, and are capable of clamping the scapha of the auricle from both sides between tip end portions of the first member and the second member, and
  the measurement means includes a light emitting element that is disposed on the first sensor support portion and that radiates light, and a light receiving element that is disposed on the second sensor support portion, wherein the light emitting element and the light receiving element are located at opposite end portions of the base end portion of the second member, in such a way as to face the light emitting element and that receives transmitted light that is radiated from the light emitting element and transmitted through a measurement target site.

8. The biological information measurement device according to claim 7, wherein
  the base end portion of the second member is joined to the first member in a rotatable manner;
  a first sensor support portion that is disposed on the base end side of the base end portion of the second member that extends in a vertical direction with respect to the base end portion of the second member, and that supports the light emitting element;
  a second sensor support portion that is disposed on the tip end side of the base end portion, of the second member in a vertical direction with respect to the base end portion of the second member, and that supports the light receiving element in a direction in which the light receiving element faces the light emitting element; and
  the tip end portion of the second member that is disposed on the tip end side of the base end portion of the second member, that extends in a same direction as the second sensor support portion, and that, in conjunction with the tip end portion of the first member, is configured to clamp the scapha of the auricle from both sides.

9. The biological information measurement device according to claim 7, wherein
  the first member includes elastic deformation means that is disposed on the tip end portion of the first member and that is configured to be elastically deformed in accordance with a shape of the scapha of the auricle when the elastic deformation means comes into contact with the scapha of the auricle.

10. The biological measurement device according to claim 7, wherein the base end portion of the second member includes a pair of slits that extend in the X-axis direction.

11. The biological measurement device according to claim 10, wherein the pair of slits penetrate the base end portion of the second member from an outer side of the second member toward an inner side surface of the second member.

12. The biological measurement device according to claim 11, wherein the pair of slits are parallel to each other.

13. The biological measurement device according to claim 11, wherein humidity generated from the auricle is discharged from inside the clip to outside the clip through the pair of slits.

14. The biological measurement device according to claim 7, wherein the tip end portion of the second member has a triangular shape.

15. The biological measurement device according to claim 14, wherein the triangular shape gradually narrows from the base end portion of the second member to the tip end portion of the second member.

16. A biological information measurement device comprising:
  a first member comprising a base end portion including a space formed at a central portion, and a second member comprising a base end portion a first sensor support portion, in a second sensor support portion the first member is joined to the second member at the base end portions in a rotatable manner and configured to be attached on a scapha of an auricle in such a way as to clamp the scapha from both sides, wherein the first sensor support portion and the second sensor support portion are respective end portions of the base end portion of the second member and extend perpendicularly from the base end portion of the second member, and wherein the first sensor support portion in the space formed at the central portion results in the first member never being prevented from rotating with respect to the second member; and
  a measurement means disposed on a portion of the second member, arranged in such a way as not to compress a helix of the auricle when the second member is attached on the scapha of the auricle, and measuring biological information of an artery running in the helix.

* * * * *